United States Patent [19]
Müller et al.

[11] Patent Number: 5,166,076
[45] Date of Patent: Nov. 24, 1992

[54] DEVICE AND METHOD FOR SAMPLE DOSING IN GAS CHROMATOGRAPHY

[75] Inventors: Friedhelm Müller, Linkenheim, Fed. Rep. of Germany; Fernand Clauss, Beinheim, France

[73] Assignee: Siemens Aktiengesellschaft, Berlin & Munich, Fed. Rep. of Germany

[21] Appl. No.: 477,994
[22] PCT Filed: Oct. 17, 1988
[86] PCT No.: PCT/DE88/00640
§ 371 Date: Apr. 23, 1990
§ 102(e) Date: Apr. 23, 1990
[87] PCT Pub. No.: WO89/03990
PCT Pub. Date: May 5, 1989

[30] Foreign Application Priority Data
Oct. 22, 1987 [DE] Fed. Rep. of Germany ....... 3735814

[51] Int. Cl.$^5$ ............................................ G01N 30/20
[52] U.S. Cl. .................................... 436/161; 422/88; 422/89; 73/19.02; 73/23.24; 73/23.27
[58] Field of Search ................ 436/161; 422/103, 83, 422/88, 89; 73/19.02, 23.21, 23.24, 23.27

[56] References Cited
U.S. PATENT DOCUMENTS
3,077,766 2/1963 Reinecke ............................. 73/23
4,442,217 4/1984 Deans .................................. 436/161

FOREIGN PATENT DOCUMENTS
0049440 4/1982 European Pat. Off. .
0112407 7/1984 European Pat. Off. .
1909703 9/1969 Fed. Rep. of Germany .
1917723 10/1969 Fed. Rep. of Germany .
2040133 2/1971 Fed. Rep. of Germany .

Primary Examiner—James C. Housel
Assistant Examiner—David Redding
Attorney, Agent, or Firm—Kenyon & Kenyon

[57] ABSTRACT

A dosing device has a flow divider connected between a carrier gas source and a gas chromatography separating column, in particular a capillary column. The flow divider has a conduit with an opening and a chamber surrounding said conduit with a delivery line for the gas sample. The gas sample is taken from the sampling gas source through a metering valve with a metering loop at low pressure and passed, together with the carrier gas at higher pressure, into the flow divider. A pressure drop can be reversed by means of a reversing valve connected to the carrier gas source so that in a first switching position the sample can enter the chamber and in a second switching position a fraction of the sample corresponding to the dividing ratio in the flow divider can pass through the opening in the conduit into the separating column.

14 Claims, 2 Drawing Sheets

DEVICE AND METHOD FOR SAMPLE DOSING IN GAS CHROMATOGRAPHY

The invention relates to devices and methods for sample dosing in gas chromatography.

PRIOR ART

The efficiency of gas-chromatographic analysis depends to a large extent on the charging of the sample [dosing] into the separation column. "Slugs" of sample gas that are delimited as sharply as possible are required in the stream of carrier gas, which flows with a flow velocity that is ideal for the respective separation column. Since in practice, the pressure in the sample gas source often lies at a level that is lower than the required operating pressure for the carrier gas, pressure surges occur during sample dosing, which adversely affect the analysis results. Therefore, pumps must be provided to bring the pressure in the sample supply line (leading) to the dosing mechanism up to the required level. When capillary separation columns are used, a flow divider is provided, which makes it possible to dose [quantitatively regulate] a very small sample quantity. Such a configuration is described, for example, in the U.S. Pat. No. 4,442,217.

In the case of this known configuration, dosing into a separation column is accomplished by switching a carrier gas stream at a junction, from which a sample injection limb leads out on one side and a vent limb on the other side. With the help of restrictions to flow, flow rate ratios are adjusted so that the flow rate in an inlet line is greater than the flow rate in the sample injection limb, but smaller than that in the vent limb. This achieves that in a first switch position of a changeover switch, the carrier gas flows via a supply injection limb through the separation column, and the sample flows off through the vent limb, while in a second switch position, a small portion of the sample is conveyed through a flow divider into the separation column, and the remaining sample quantity is discharged. The flow divider consists of a conduit, having an inlet connectable to the carrier gas source and having an outlet which is connected to the supply injection limb leading to the separation column. This conduit is surrounded by a cylindrical chamber and is provided with a centrical opening. On its upper end, the cylindrical chamber is provided with a connection for the inlet limb. On its lower end with a connection for the carrier gas and with a connection for the vent limb. The junction is formed through an opening in the conduit within the chamber. In the case of this known configuration as well, subject to function, the pressure in the sample supply line must be the same or higher than the carrier gas pressure.

Thus the task consists in creating a device for sample dosing, which will enable the samples to be charged independently of the pressure existing in the sample gas source.

DESCRIPTION OF THE INVENTION

The task is able to be solved with a device that has a carrier gas source of a constant and adjustable pressure, a two-way reversing valve, whose inlet is connected via a conduit to the carrier gas source, and a branch line connected to an outlet of the reversing valve. Additionally, the present invention has a flow divider including a tubing connected to the branch line, with an opening and a chamber surrounding the tubing and extending upstream and downstream from the opening. The present invention also has a conduit section connected to the output of the tubing and leading to the separation column. A branch line is connected to the second outlet of the reversing valve and discharges into the downstream part of the chamber. An outgoing line has an adjustable resistance to flow and emanates from the downstream part of the chamber. A supply line is provided for the sample that has an adjustable resistance to flow and which discharges into the upper, upstream end section of the chamber. The flow resistances are dimensioned so that the volumetric flow rate ($Q11$) in the supply line is less than the flow rate ($Q10$) through the outgoing line, but is greater than the flow rate ($Q4$) into the separation column. The present invention also includes a dosing valve with six connections ($a1$-$a6$), a conduit leading from the sample gas source to the first connection ($a1$) of the dosing valve, an outgoing valve that leads off from the second connection ($a2$), a dosage volume that communicates with the remaining connections ($a3$-$a6$) by its ends, a conduit that leads from the gas source to the fifth connection ($a5$), and a sample supply line that communicates with the fourth connection.

By using a dosing valve known per se with sample volumes (c.f. for example U.S. Pat. No. 3,077,766, FIG. 4 to 7), the sample can be easily supplied to the flow divider of the dosing mechanism, completely independently from the pressure in the sample gas source.

Another important advantage lies in the fact that one can select the time interval for the sample dosing into the separation column to be shorter than the time interval of the sample charging from the dosage volume of the dosing valve.

In this manner, the errors that occurred previously due to adsorption or desorption during the application of the known dosing valve with dosage volumes are largely avoided.

The sample volume to be dosed [quantitatively regulated] can be easily adjusted and thus be adapted to the capacity of the separation column. This is particularly significant for the application of capillary columns.

BRIEF DESCRIPTION OF DRAWINGS

To clarify the invention, a device according to the invention is depicted schematically in FIG. 1.

DESCRIPTION OF THE PREFERRED EMBODIMENTS

Figure 1:
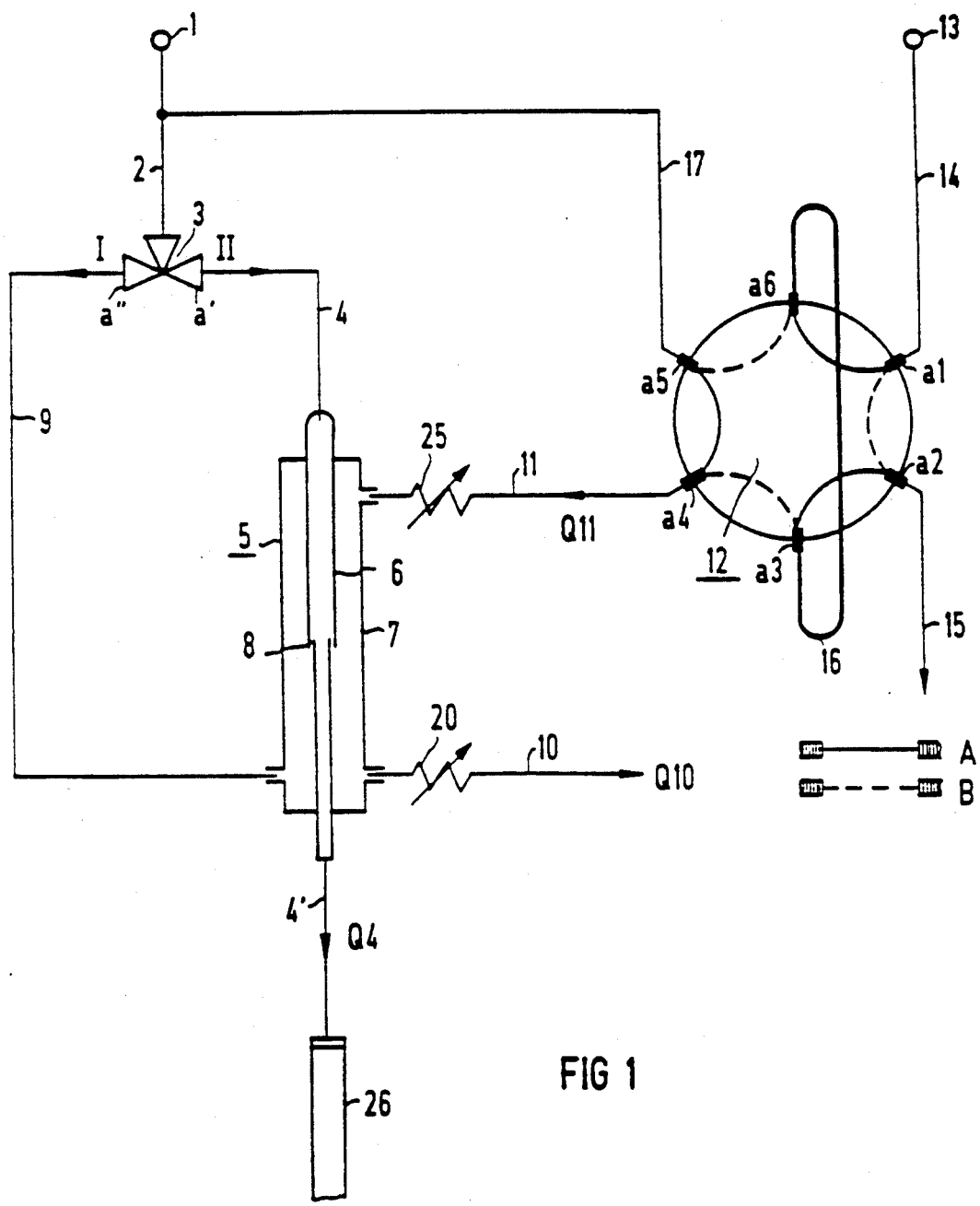

A carrier gas source 1 having an adjustable, constant pressure is connected via a conduit for carrier gas supply 2 to the inlet of a two-way reversing valve 3.

A first branch line 4 leads from the first outlet a' of the reversing valve 3 to a flow divider 5 and, from there, via another branch line 4' to the separation column 26.

The flow divider 5 consists of a tubing 6 switched between the branches line 4 and 4' that is surrounded by a chamber 7 and has a centrical opening 8, preferably in the shape of an annular gap.

The second outlet a" of the reversing valve 3 is connected to a second branch line 9, that discharges into the downstream end section of the chamber 7. An outgoing line 10 provided with an adjustable resistance to flow, for example a needle valve 20, likewise issues from the downstream section of the chamber 7.

The sample supply line 11, which is likewise provided with an adjustable resistance to flow 25, discharges into the upper, that is the upstream end section of the chamber 7.

The resistances to flow in the conduits 4, 10 and 11 are to be dimensioned so that $$Q10 > Q11 > Q4 \quad (1)$$

whereby

Q11 is the volumetric flow rate in the sample supply line 11;
Q10 is the flow rate through the outgoing line 10 and
Q4 is the flow rate through the separation column 26.

A dosing valve 12 of a known type of construction has six connections a1 to a6.

In a first switch position A (connections drawn with a solid line), the sample stream from the sample gas source 13 is conveyed via the conduit 14 to the connection a1 and, from there, via the sample volume 16, in this case in the form of a dosage loop, situated between the connections a3 and a6, to the outgoing line 15 that communicates with the connection a2.

A third branch line 17 connected to the carrier gas supply line 2 conveys carrier gas through the connection a5 to the connection a4 and into the sample supply line 11 leading to the chamber 7.

If the reversing valve 3 in the switch position II is switched to the branch line 4, then the carrier gas will flow both through the flow divider 5 into the separation column 26 and also through the conduit 17, the dosing valve 12 and the sample supply line 11 into the chamber 7 and, from there, it will flow off, together with the carrier gas portion flowing out of the opening 8, through the conduit 10.

After the dosing valve 12 is switched over into its second switch position B (connections drawn with dotted lines), the contents of the sample volume 16 is conveyed, with the help of the stream of carrier gas supplied via the connection a5, by way of the supply line 11 into the chamber 7. Since Q11<Q10, the difference Q10−Q11 flows out of the tubing 6 that is pressurized with full carrier gas pressure, through the opening 8 into the chamber 7 and passes, together with the sample, by way of the outgoing line 10 into the open. One must make sure thereby that the diffusion rate of the sample is less than the discharge rate of the carrier gas emerging from the opening 8, to prevent any sample from attaining the separation column 26 via the conduit 4'.

If the reversing valve 3 is switched into the switch position I and thus to the branch line 9, a portion of the sample volume flowing through the chamber 7 moves, through the opening 8 into the conduit section 4' leading to the separation column 26, while the excess portion of the sample—in the case of capillary columns that is more or less 90% of the content of the sample volume 16—is carried away, together with the carrier gas, from the branch line 9 by way of the outgoing line 10.

The time span Δt1, during which the dosing valve 12 is in the second switch position B, is selected to be longer than the time span Δt2, during which the reversing valve 3 is in the switch position I. The reversing valve 3 and the dosing valve 12 are switched in a way which will allow the time span Δt2 to lie within the time span Δt1. With this operating method, one advantageously avoids the disturbances in the analysis caused by the possible mixing and carrying over of the gas sample [resulting] from adsorption and diffusion occurrences in the dosing valve 12 and in the sample volume 16. Also, as a result of the heart cutting with sharp dosage limitations, an optimum peak form is achieved in the analysis result.

In practice, it turns out that it is a relatively difficult and long-drawn-out procedure to measure and adjust the gas flow rates Q4, Q10, Q11, which according to equation (1) are important for the functioning of the dosing mechanism.

Figure 2:
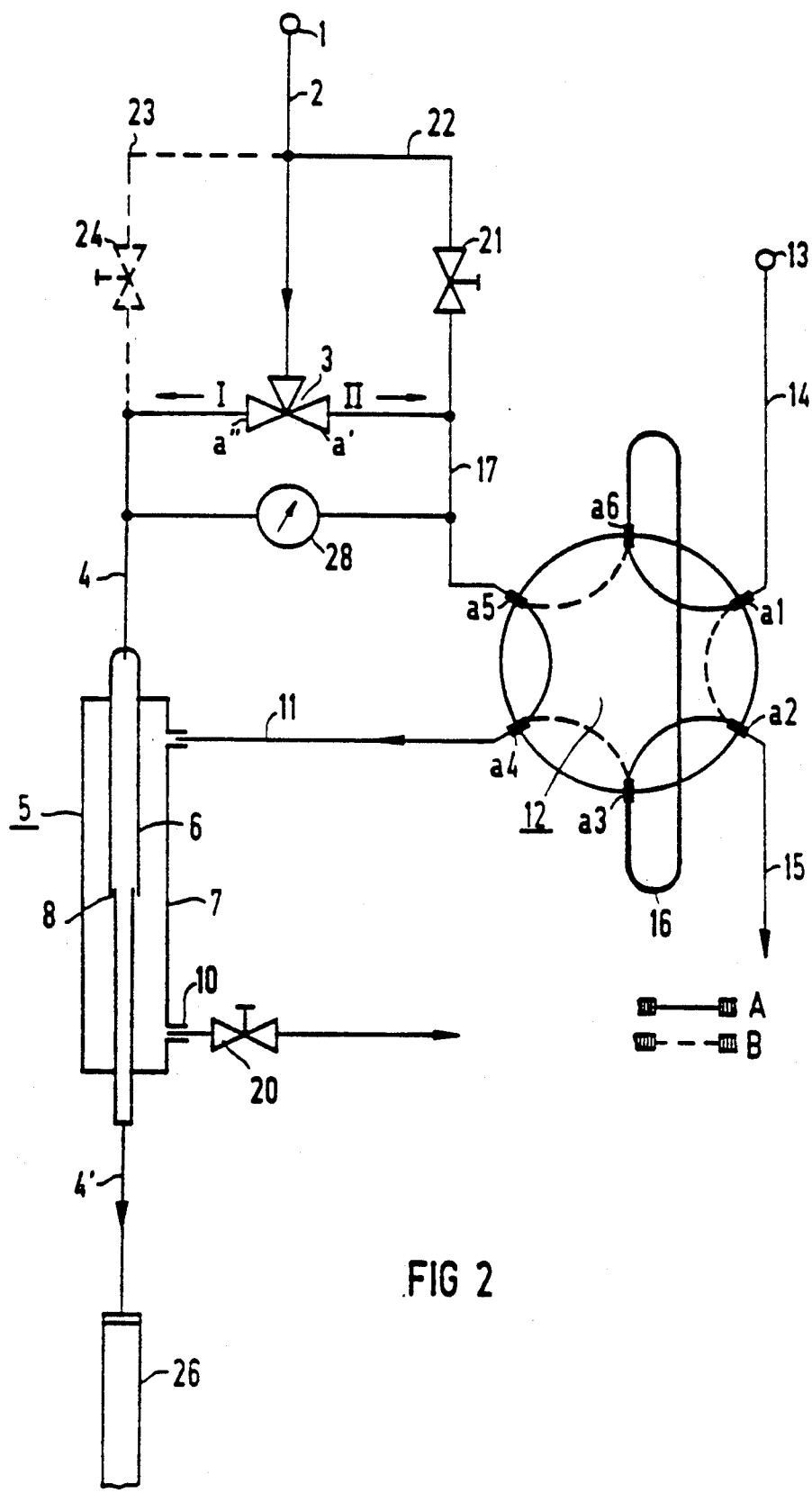
FIG. 2 illustrates another improved specific embodiment of the invention.

Therefore, another refinement of the invention solves the task of creating a dosing mechanism, which has a flow divider and a dosing valve and can be operated without measuring and adjusting volumetric flow rates. A specific embodiment is schematically depicted in FIG. 2 and described in the following. The parts that conform with the corresponding parts in FIG. 1 are given the same reference numerals.

The stream of carrier gas of a constant and adjustable pressure coming from the carrier gas source 1 is supplied via a conduit 2 to the inlet of a two-way reversing valve 3 with a first outlet a' and a second outlet a''. A conduit 4, which leads through the tubing 6 of the flow divider 5 to the separation column 26, communicates with the second outlet a'''.

As already described, the flow divider 5 consists of a tubing 6 that is surrounded by a chamber 7 and has a central, annular-gap-shaped opening 8. The supply line 11 for the sample discharges into the upper, upstream end section of the chamber 7. An outgoing line 10, in which is mounted a needle valve 20, issues from the lower, downstream end of the chamber 7.

A dosing valve 12 of a known type of construction is provided with six connections a1 to a6.

The sample gas source 13 communicates via the conduit 14 with the connection a1. The sample gas source is connected via the conduit 14 to the connection a1. An exhaust 15 is switched to the connection a2. A sample volume 16 in the form of a dosage loop communicates by both of its ends with the connections a3 and a6.

The sample supply line 11 that communicates with the connection a4 leads into the chamber 7. The connection a5 communicates via the conduit 17 with the first outlet a' of the reversing valve 3. The operating method of the device is as follows:

In a first switching phase, the reversing valve 3 is in the switch position II; the dosing valve 12 is in the switch position A. The stream of carrier gas from the carrier gas source 1 flows through the conduit 4 and the tubing 6 of the flow divider 5, partially into the separation column 26, which it then flushes. The larger portion of the stream of carrier gas moves through the annular-gap-shaped opening 8 into the chamber 7 and from there, it flows off, together with a stream of carrier gas that is conveyed through a conduit 22 containing a needle valve 21 and through the supply line 11, through the outgoing line 10.

For sampling [purposes], the sample gas stream that flows out of the sample gas source 13 through the conduit 14 is switched via the connections a1 and 16 to the sample volume 16. It then flows off from there via the connection a2 into the conduit 15.

In a second switching phase, the dosing valve is switched to the switch position B during a time span Δt1. Now, with the help of the carrier gas supplied via the conduits 22 and 17, the sample located in the sample volume 16 is pushed out into the chamber 7. There it emerges, together with the carrier gas issuing from the opening 8, through the outgoing line 10.

In a third switching phase, the reversing valve 3 is switched during a time span Δt2 into the switch position II and thus to the branch line 17. The sample located in the chamber 7 is pushed out through the opening 8 into the tubing 6 and, from there, dosed [quantitatively regulated] into the separation column. In this case as well, Δt1>Δt2, whereby Δt2 lies within Δt1.

To ensure, during the various switching phases, that the dead spots are flushed and to prevent the sample gas from diffusing upstream into the conduit 4, a bypass line 23, which connects the carrier gas conduit to the conduit 4, can be provided with a needle valve 24. By means of a differential-pressure meter 28 connected between conduits 4 and 17, in the various switching phases, one can monitor the reversal of the streams of carrier gas due to changes in the direction of the pressure difference.

We claim:

1. An apparatus for dosing samples of sample gas for gas-chromatographic analysis independently of the pressure of the source of sample gas comprising:
   a) a carrier gas source constructed so as to deliver gas at an adjustable pressure;
   b) a two-way reversing valve, having an inlet, a first outlet, and a second outlet;
   c) a first conduit connecting the inlet of the two-way reversing valve to the carrier gas source, and having a first flow resistance;
   d) a flow divider including:
      (i) a tubing having an inlet and an opening at an outlet; and
      (ii) a chamber surrounding the tubing and having an upper part extending up from the opening of the tubing and having a lower part extending down from the opening of the tubing;
   e) a first branch line connecting the first outlet of the two-way reversing valve, with the inlet of the tubing and having a second flow resistance;
   g) a separation column;
   f) a second conduit connecting the outlet of the tubing of the flow divider with the separation column;
   h) a second branch line connecting the second outlet of the two-way reversing valve with the lower part of the chamber;
   i) a first outgoing line constructed so as to have a first adjustable flow resistance and connected to the lower part of the chamber;
   j) a third conduit having a first end and a second end, said first end being connected to a sample gas source;
   k) a second outgoing line having a first end and a discharge end;
   l) a fourth conduit having a first end and a second end, said first end being connected to the carrier gas source; and
   m) a supply line constructed so as to have a second adjustable flow resistance and having a first end and a second end, said first end being connected to said upper part of said chamber,
   n) a dosing valve having a sample volume and constructed so as to be switchable between a first state and a second state,
   wherein when said dosing valve is in said first state said dosing valve is in fluid communication with said second end of said third conduit and with said first end of said second outgoing line such that said sample volume of the dosing valve accepts said sample gas, and
   wherein when said dosing valve is in said second state said dosing valve is in fluid communication with said second end of said fourth conduit and with said second end of said supply line.
   whereby said first adjustable flow resistance, said second adjustable flow resistance, said first flow resistance, and said second flow resistance are dimensioned to produce a volumetric flow rate Q11 in said supply line that is less than a flow rate Q10 through said first outgoing line and is greater than a flow rate Q4 into said separation column and said device is operable when the pressure of the supply of sample gas is lower than the pressure of the carrier gas source.

2. An apparatus for dosing samples of sample gas for gas-chromatographic analysis independently of the pressure of the source of sample gas comprising:
   a) a carrier gas source constructed so as to deliver gas at an adjustable pressure;
   b) a two-way reversing valve, having an inlet, a first outlet, and a second outlet;
   c) a first conduit connecting the inlet of the two-way reversing valve to the carrier gas source;
   d) a flow divider having:
      (i) a tubing having an inlet and a centrally disposed opening at an outlet; and
      (ii) a chamber surrounding the tubing and having an upper part extending up from the opening of the tubing and having a lower part extending down from the opening of the tubing;
   e) a branch line connecting the second outlet of the two-way reversing valve with the inlet of the tubing;
   f) a first outgoing line connected to said lower part of said chamber;
   g) a separation column;
   h) a second conduit connecting said outlet of said tubing of said flow divider with said separation column;
   i) a third conduit having a first end and a second end, said first end being connected to a sample source;
   j) a second outgoing line having a first end and a discharge end;
   k) a fourth conduit having a first end and a second end, said first end being connected to said first outlet of the two-way reversing valve; and
   l) a dosing valve having a sample volume and constructed so as to be switchable between a first state and a second state; and
   m) a supply line having a first end and a second end, said first end being connected to said upper part of said chamber,
   wherein when said dosing valve is in said first state said dosing valve is in fluid communication with said second end of said third conduit and with said first end of said second outgoing line such that said sample volume of the dosing valve accepts said sample gas,
   and wherein when said dosing valve is in said second state said dosing valve is in fluid communication with said second end of said fourth conduit and with said second end of said supply line; and
   n) a first bypass line having a first needle valve and connecting the inlet of the two-way reversing valve to the first outlet of the two-way reversing valve.

3. A device according to claim 2, further comprising a second bypass line having a second needle valve, said second bypass line connecting the inlet of the two way reversing valve to the second outlet of the two-way reversing valve.

4. The apparatus of claim 3 wherein said first outgoing line connected to lower part of the chamber includes a needle valve.

5. The apparatus of claim 3, further comprising a differential pressure meter coupled between the branch line and the fourth conduit, and monitoring a differential pressure between the branch line and the fourth conduit.

6. A method for supplying a sample of sample gas from a sample gas source to a separation column for gas-chromatographic analysis, comprising the steps of:
  a) placing a sample volume in fluidic communication with the sample gas source to fill the sample volume with sample gas and supplying carrier gas from a source of carrier gas to an inlet of a tubing of a flow divider disposed within a chamber of the flow divider, the chamber having an outlet, the tubing having an opening therein in communication with the chamber and an outlet end in communication with a separation column, the carrier gas being supplied to the separation column at a first flow rate; the gas flows through the outlet of the chamber at a second flow rate;
  b) fluidically isolating the sample volume from the sample gas source and placing the sample volume in fluidic communication with the carrier gas source and with the chamber;
  c) forcing the sample gas from the sample volume to the chamber with the carrier gas at a third flow rate; and
  d) interrupting the supply of carrier gas source to the tubing and supplying carrier gas from the carrier gas source to the chamber, the flow rates being such that a portion of the sample gas flows through the opening of the tubing out the outlet end thereof and into the separation column when carrier gas is supplied to the chamber and no sample gas flows through the opening of the tubing when carrier gas is supplied to the inlet of the tubing.

7. The method according to claim 6, further comprising the steps of:
  e) interrupting the supply of carrier gas to the chamber and resuming the supply of carrier gas to the inlet of the tubing; and
  f) resuming fluidic communication between the sample volume and the sample gas source and fluidically isolating the sample volume from the carrier gas source and the chamber.

8. The method according to claim 6, wherein the flow rates during the performance of step c are such that the rate of discharge of carrier gas from the opening of the tubing is greater than a rate of diffusion of the sample gas into the opening of the tubing.

9. The method according to claim 7, further comprising cyclically repeating steps a) through f).

10. The method according to claim 7, wherein a first predetermined time elapses between the performance of step d) and the performance of step e) and a second predetermined time elapses between the performance of step c) and the performance of step f), the first predetermined time being less than, and occurring within, the second predetermined time.

11. A method for supplying a sample of sample gas from a sample gas source to a separation column for gas-chromatographic analysis, comprising the steps of:
  a) placing a sample volume in fluidic communication with the sample gas source to fill the sample volume with sample gas and supplying carrier gas from a source of carrier gas to an inlet of a tubing of a flow divider disposed within a chamber of the flow divider, the tubing having an opening therein in communication with the chamber and an outlet end in communication with a separation column, the carrier gas being supplied to the inlet of the tubing and the chamber;
  b) fluidically isolating the sample volume from the sample gas source and placing the sample volume in fluidic communication with the carrier gas source and with the chamber;
  c) forcing the sample gas from the sample volume to the chamber, the ratio of pressures in the tubing and in the chamber being such that carrier gas flows through the opening from the tubing into the chamber;
  d) modifying the supply of carrier gas source to the inlet of the tubing and to the chamber so that the ratio pressures in the tubing and in the chamber being such that a portion of the sample gas flows through the opening to the outlet end of the tubing and into the separation column.

12. The method according to claim 11, further comprising the steps of:
  e) modifying the supply of carrier gas to the inlet of the tubing and the chamber so that the pressures in the tubing and the chamber are resumed such that the carrier gas flows from the tubing through the opening of the tubing into the chamber; and
  f) resuming fluidic communication between the sample volume and the sample gas source and fluidically isolating the sample volume from the carrier gas source and the chamber.

13. The method according to claim 12, further comprising cyclically repeating steps a) through f).

14. The method according to claim 12, wherein a first predetermined time elapses between the preformance of step d) and the performance of step e) and a second predetermined time elapses between the preformance of step c) and the performance of step f), the first predetermined time being less than, and occurring within, the second predetermined time.

* * * * *